United States Patent [19]

Samans et al.

[11] 3,985,776

[45] Oct. 12, 1976

[54] STANNOUS STABILIZATION OF MALEIC ANHYDRIDE

[75] Inventors: Cecelia Samans, Chicago; Martin R. Spatz, Lisle, both of Ill.

[73] Assignee: Standard Oil Company (Indiana), Chicago, Ill.

[22] Filed: July 21, 1975

[21] Appl. No.: 597,360

[52] U.S. Cl. .......................................... 260/346.8 R
[51] Int. Cl.² ..................................... C07D 307/60
[58] Field of Search .................................. 260/346.8

[56] References Cited
UNITED STATES PATENTS 3,775,436   11/1973   Stenseth ..................... 260/346.8 M

FOREIGN PATENTS OR APPLICATIONS 7,100,007   1/1971   Japan ............................. 260/346.8

*Primary Examiner*—Harry I. Moatz
*Attorney, Agent, or Firm*—William H. Magidson; Arthur G. Gilkes; William T. McClain

[57] ABSTRACT

Stabilization of maleic anhydride with stannous compounds, such as stannous chloride and stannous salts of aliphatic monocarboxylic acids.

8 Claims, No Drawings

STANNOUS STABILIZATION OF MALEIC ANHYDRIDE

This invention relates to the heat stabilization of maleic anhydride with stannous compounds. More particularly, this invention relates to the stabilization of maleic anhydride with stannous salts of aliphatic monocarboxylic acids.

The literature is replete with patents directed to the stabilization of maleic anhydride since maleic anhydride is heat and light sensitive, i.e. it yellows with time and temperature. For the most part, the extent of yellowing depends on the quality of the maleic anhydride as well as the conditions of storage. While the mechanism and cause of the yellowing is not known, this yellowing has been blamed on parts per million level of impurities (reaction and/or processing contaminants and/or by-products) which may react themselves to give yellow impurities or catalyze the degradation of the maleic anhydride.

Normally, commercial maleic anhydride must pass two molten color specifications. The initial color of the maleic anhydride melt must be below a certain accepted value and the maleic anhydride melt must be heat stable for 2 hours at 140° C. Since maleic anhydride is sold in solid form, as briquettes, tablets and pastilles, and in the molten form at around 60° C, the maleic anhydride must pass these color specifications, not only after manufacture, but also after extended storage and transportation at 60° C. Further, since chemical additives themselves are incapable of improving off color maleic anhydride, maleic anhydride being stabilized must be of reasonably high quality.

The literature in many cases indicates contradictory results with the same stabilizers. The reason for this is not understood at this time but may be related to the history or method of producing the particular maleic anhydride since maleic anhydride can be produced by oxidation of benzene, saturated and unsaturated $C_4$ hydrocarbons (e.g. butane or butene) or as a by-product of naphthalene oxidation to phthalic anhydride. For example, while Halcon U.S. Pat. No. 3,586,704 indicates that sodium iodide is ineffective, Monsanto British specification 1,331,853 discloses the stabilization of maleic anhydride with halogen compounds broadly and illustrates the effectiveness of sodium iodide as a stabilizer for maleic anhydride, (both of these references are incorporated by reference). Our own studies seem to confirm the conclusions of the Halcon Patent. As indicated above, the reason for these discrepancies is unclear and may be related to the method of producing the maleic anhydride, etc.

The general object of this invention is to provide a new class of heat stabilizers for maleic anhydride. Other objects appear hereinafter.

We have now found that maleic anhydride can be heat stabilized with stannous compounds. For the purpose of this invention, the terms "heat stabilized" or "heat stable" are used to indicate that other things being equal, the maleic anhydride containing stannous compound has a lower APHA (American Public Health Association Units in accordance with ASTM D1209-69) after being held at 140° C for 2 or more hours than maleic anhydride containing no stannous stabilizer. The stannous stabilizers useful in this invention include any stannous compound capable of providing the aforesaid improvement.

Suitable stannous compounds include stannous salts of carboxylic acids including any of those described in U.S. Pat. No. 3,032,571, which is incorporated by reference such as stannous acetate, stannous octoate, stannous oleate, etc.; stannous salts of inorganic acids, such as stannous bromide, stannous chloride, stannous sulfate, stannous pyrophosphate, etc.; stannous oxide, etc. The preferred stannous compounds useful in this invention are stannous chloride and stannous salts of aliphatic (hydrocarbyl) monocarboxylic acids containing 8 to 24 carbon atoms, such as stannous 2-ethylhexanoate, stannous octoate, stannous neodecanoate, stannous oleate, stannous stearate, stannous palmitate, stannous tetracosanate, etc. Of these preferred stannous salts, liquid stannous salts of aliphatic monocarboxylic acids (at ambient temperatures) are particularly preferred since these compounds can be added more conveniently to molten maleic anhydride on a commercial scale whereas stannous chloride should be added in a solution, such as in dimethyl sulfoxide, in order to get uniform distribution of the relatively low concentration of stabilizer in the molten maleic anhydride.

As indicated in U.S. Pat. No. 3,032,571 stannous salts are subject to degradation when exposed to the air and for purposes of this invention, it is essential that the stannous salts be utilized in the undegraded form. Generally speaking, the degraded stannous salts are not as effective as the undegraded salts because of dilution with inactive stannic compounds. The commercially available, so-called stabilized stannous salts of carboxylic acids, sold as catalysts for polyurethane foam products, are especially efficacious since these compounds are in an undegraded form, usually due to the presence of a suitable antioxidant such as 4-tert-butyl catechol. The antioxidant can be present on a concentration of 0.01 to 2% by weight of the stannous compound.

The stannous salts can be used in a stabilizing concentration of about 1 to 2,000 ppm based on the concentration of maleic anhydride. Generally the preferred stannous salts can be utilized in a concentration of about 5 to 200 ppm based on the weight of maleic anhydride. However, larger concentration can be added without degrading the maleic anhydride or reducing the subsequent rate of esterification of the maleic anhydride. It is generally recognized that stannous salts, particularly stannous salts of aliphatic carboxylic acids, are useful esterification catalysts.

The maleic anhydride utilized in this invention can be produced by any process suitable for the production of maleic anhydride. However, we prefer to use maleic anhydride produced by the oxidation of butane, such as that described in Boghosian U.S. Pat. No. 3,862,146, which is incorporated by reference. In any case, maleic anhydride should be relatively pure prior to the addition of the stabilizer. Generally, the stabilizer can be added to molten maleic anhydride shortly after the maleic anhydride is distilled from most of its impurities and by-products formed in the oxidation of the particular organic precursor.

The anhydrous stabilizer can be added to the maleic anhydride neat or in a diluted form. On a commercial basis dilution of the preferred liquid stannous salts of aliphatic carboxylic acids is not necessary. However, if desired, the stannous salts can be dissolved in an aromatic hydrocarbon, such as ortho-xylene, para-xylene, meta-xylene, toluene, etc. In the case of solid stannous salts, it is generally best to dissolve the salt in an appropriate solvent in order to get uniform distribution of the salt in the maleic anhydride. As indicated above, dimethyl sulfoxide is an excellent solvent for stannous chloride.

The following examples are merely illustrative and should not be construed as limiting the scope of the invention.

EXAMPLE I

After 60 grams of solid maleic anhydride produced by the method of U.S. Pat. No. 3,862,146 was placed in a 50 milliliter/tall-form Nesslerimeter tube, 100 ppm of stabilizer (0.0060 grams neat) was added to the maleic anhydride at room temperature. The maleic anhydride in the Nesslerimeter test tube was melted rapidly in a 140° C tube-block-heater and the mixture blended. Excess maleic anhydride melt was removed leaving a constant 8 inch high liquid level. Immediately thereafter the initial molten color was measured by visual comparison with standard APHA solutions in Nesslerimeter tubes according to ASTM D 1209-69 (platinum-cobalt scale). After reading, the tube was placed in the 140° C heater and capped with a 10-milliliter beaker to prevent contamination and the tube heater was covered with a 100 × 190 millimeter crystallization dish. The heat stable colors were read after 2, 4 and 24 hours. The results are set forth below in Table I. Multiple numbers in the Table indicates the range of colors measured for repeat tests.

Table I

| Stabilizer | Molten Color APHA | | | |
|---|---|---|---|---|
| | Initial | 2 | Hours at 140°C 4 | 24 |
| None | 20/30 | 60/90 | 80/100 | 250/900 |
| Stannous Stearate | 20 | 30 | 30/35 | 70/80 |
| Stannous Oxide | 25 | 50 | 60 | 150 |
| Stannous Bromide | 40 | 60 | 80 | 250 |
| None | 0/10 | 150/200 | 250/300 | >1500 |
| Stannous Chloride | 10 | 35 | 45 | 80 |

The above data indicates that stannous compounds, particularly stannous chloride and stannous salts of aliphatic monocarboxylic acids are effective heat stabilizers of maleic anhydride.

When the concentration of stannous stearate was reduced to 10 ppm, the initial color, 2 hour, 4 hour and 24 hour values were 20, 30, 35 and 100, respectively.

EXAMPLE II

This example illustrates the heat stabilization of a different sample of maleic anhydride produced by the method of U.S. Pat. No. 3,862,146 using 50 ppm stabilizer. Example I was repeated using half as much stabilizer. The results are set forth below in Table II:

Table II

| Stabilizer | Molten Color APHA | | | |
|---|---|---|---|---|
| | Initial | 2 | Hours at 140°C 4 | 24 |
| None | 20/30 | 90/150 | 125/300 | 500/>1500 |
| Stannous Stearate | 25 | 45/50 | 60/90 | 150/400 |
| Stannous Octoate | 30 | 50 | 60 | Not run |
| Stannous Laurate | 25 | 60 | 90 | 400 |
| Stannous Oxide | 30 | 70 | 80 | 600 |

EXAMPLE III

Example I was repeated using a different batch of maleic anhydride prepared by the method of U.S. Pat. No. 3,862,146 using 100 p.p.m. stabilizer. The stabilizers were added after the maleic anhydride had been held at 63° C for about 100 hours. The results are set forth below in Table III:

Table III

| Stabilizer | Molten Color APHA | | | |
|---|---|---|---|---|
| | Initial | 2 | Hours at 140°C 4 | 24 |
| None | 15 | 35/40 | 45/70 | 250/700 |
| Stannous Oleate | 15 | 25 | 30 | 150 |
| Stannous Octoate | 15 | 25 | 35 | 200 |
| Stannous Neodecanoate | 15 | 25 | 35 | 150 |

EXAMPLE IV

Example I was repeated using a commercially available unstabilized maleic anhydride which is produced in Spain by the oxidation of benzene. The results are set forth below in Table IV:

Table IV

| Stabilizer | Molten Color APHA | | | |
|---|---|---|---|---|
| | Initial | 2 | Hours at 140°C 4 | 24 |
| None | 40/60 | 350/>1500 | 1000/>1500 | 1300/>1500 |
| Stannous Stearate | 40 | 60 | 90 | 300 |
| Stannous Oleate | 45 | 60 | 80 | 700 |
| Stannous Neodecanoate | 50 | 70 | 80 | 1300 |
| Stannous Pyrophosphate | 45 | 125 | 200 | 1000 |

EXAMPLE V

This example illustrates the effect of storage on the stabilization of maleic anhydride having an initial APHA of 0. Forty p.p.m. of a commercially available stannous oleate containing a stabilizing concentration of 4-tert-butyl catechol was added as a 50 weight percent solution of orthoxylene to 300 ml maleic anhydride produced according to U.S. Pat. No. 3,862,146. Stabilized and unstabilized samples were stored under nitrogen prior to molten color measurements. The details of the experiments and results are set forth below in Table V.

Table V

| | Storage Exposure | | | Molten Color, APHA | | | |
|---|---|---|---|---|---|---|---|
| | Days | °C | Other Conditions | Initial | 2 | Hours at 140°C 4 | 24 |
| Unstabilized | 1 | 63 | Dark Room | 0 | 20 | 35 | 300 |
| Stabilized | 1 | 63 | Dark Room | 0 | 10 | 20 | 125 |
| Unstabilized | 2 | 63 | Dark Room | 0 | 15 | — | 200 |
| Stabilized | 2 | 63 | Dark Room | 0 | 10 | — | 90 |
| Unstabilized | 5 | 63 | Dark Room | 0 | 25 | 45 | 450 |
| Stabilized | 5 | 63 | Dark Room | 0 | 20 | 30 | 100 |
| Unstabilized | 2 | 20 | Dark Room | 0 | 15 | — | 250 |
| Stabilized | 2 | 20 | Dark Room | 0 | 10 | — | 125 |

Table V-continued

| | Storage Exposure | | Other Conditions | Molten Color, APHA | | | |
|---|---|---|---|---|---|---|---|
| | Days | °C | | Initial | 2 | 4 | 24 |
| | | | | | Hours at 140°C | | |
| Unstabilized | 5 | 20 | Dark Room | 5 | 50 | 90 | 450 |
| Stabilized | 5 | 20 | Dark Room | 5 | 25 | 35 | 100 |
| Unstabilized | 2 | 20 | Lab Light | 5 | 20 | — | 250 |
| Stabilized | 2 | 20 | Lab Light | 5 | 15 | — | 125 |
| Unstabilized | 5 | 20 | Lab Light | 5 | 70 | 100 | 250 |
| Stabilized | 5 | 20 | Lab Light | 5 | 30 | 45 | 150 |

The above data illustrates that stannous oleate is an effective heat stabilizer of high purity maleic anhydride.

We claim:

1. A composition comprising maleic anhydride and a heat stabilizing concentration of at least one stannous compound selected from the group consisting of stannous bromide, stannous chloride and stannous salts of aliphatic monocarboxylic acids containing 8 to 24 carbon atoms.

2. The composition of claim 1, wherein said stannous salt comprises stannous chloride in a concentration of 1 to 2000 ppm based on the concentration of maleic anhydride.

3. The composition of claim 1 wherein said stannous compound comprises a stannous salt of a liquid aliphatic monocarboxylic acid containing 8 to 24 carbon atoms.

4. The composition of claim 3, wherein said stannous salt is present in a concentration of about 1 to 2000 ppm based on the concentration of maleic anhydride.

5. The composition of claim 4, wherein said composition contains an antioxidant.

6. The composition of claim 4, wherein said stannous salt comprises stannous oleate.

7. The composition of claim 4, wherein said stannous salt comprises stannous octoate.

8. The composition of claim 4, wherein said stannous salt comprises stannous stearate.

* * * * *